United States Patent

Showell et al.

Patent Number: 5,134,146
Date of Patent: Jul. 28, 1992

[54] SUBSTITUTED OXADIAZOLES AND THIADIAZOLES FOR USE IN THE TREATMENT OF GLAUCOMA

[75] Inventors: Graham Showell, Welwyn Garden City, England; Victor Lotti, Harleysville, Pa.

[73] Assignee: Merck Sharp and Dohme Ltd., Hertfordshire, United Kingdom

[21] Appl. No.: 706,707

[22] Filed: May 29, 1991

[30] Foreign Application Priority Data

May 13, 1990 [GB] United Kingdom ............... 9012173
Nov. 26, 1990 [GB] United Kingdom ............... 9025661

[51] Int. Cl.$^5$ ............... A61K 31/44; A61K 31/415; A61K 31/445
[52] U.S. Cl. ............... 514/299; 514/305; 514/326; 514/340; 514/342; 514/361; 514/363; 514/364
[58] Field of Search ............... 514/299, 305, 326, 340, 514/342, 361, 363, 364

[56] References Cited

U.S. PATENT DOCUMENTS 5,041,455  8/1991  Sauerberg et al. ............... 514/340

FOREIGN PATENT DOCUMENTS 239309  9/1987
301729  2/1989
307140  3/1989  European Pat. Off.
307142  3/1989  European Pat. Off.
322034  6/1989  European Pat. Off.
323864  7/1989  European Pat. Off.

OTHER PUBLICATIONS

Drugs, 1979, vol. 17, pp. 38-55 (1979).

Primary Examiner—Bernard Dentz
Attorney, Agent, or Firm—Manfred Polk; Charles M. Caruso

[57] ABSTRACT

The use of compounds for formula (I):

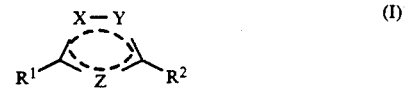

or a salt or prodrug thereof; wherein
one of X, Y, or Z is an oxygen or sulphur atom and the other two are nitrogen atoms, and the dotted circle represents two double bonds thus forming a 1,3,4-oxadiazole, 1,2,4-oxadiazole, 1,3,4-thiadiazole or 1,2,4-thiadiazole nucleus;
$R^1$ represents a non-aromatic azacyclic or azabicyclic ring system selected from

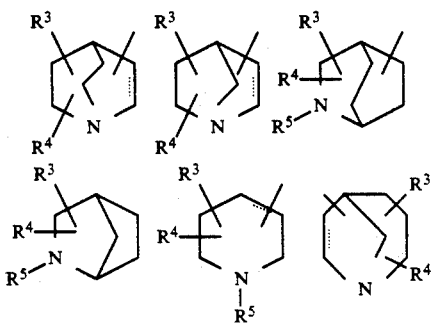

wherein the broken line represents an optional chemical bond;
the substituents $R^3$ and $R^4$ may be present at any position, including the point of attachment to the oxa- or thia-diazole ring, and independently represent hydrogen, $C_{1-4}$ alkyl, halo, $C_{1-4}$ alkoxy, hydroxy or carboxy, or $R^3$ and $R^4$ together represent carbonyl;
the group $R^5$ represents hydrogen or $C_{1-4}$ alkyl; and $R^2$ represents hydrogen, $C_{1-8}$ hydrogen, $C_{1-8}$ alkyl optionally substituted by hydroxy or fluoro, $C_{2-8}$ alkenyl, $OR^7$, $SR^7$, $NR^7R^8$, CN, $CO_2R^7$, $CONR^7R^8$ OR $NHCONHR^9$ where $R^9$ is $C_{1-4}$ alkyl; wherein $R^7$ and $R^8$ independently represent hydrogen or saturated or unsaturated $C_{1-4}$ alkyl provided that, when $R^7$ and $R^8$ in $NR^7R^8$ are both hydrogen, at least one of $R^3$ and $R^4$ is $C_{1-4}$ alkyl, in the treatment of glaucoma, novel compounds having such use, formulations containing them and their synthesis.

9 Claims, No Drawings

SUBSTITUTED OXADIAZOLES AND THIADIAZOLES FOR USE IN THE TREATMENT OF GLAUCOMA

The present invention relates to a class of substituted oxadiazoles and thiadiazoles for use in the treatment of glaucoma and to certain novel compounds having such use, formulations containing them and their synthesis.

Glaucoma is an ocular disorder associated with elevated intraocular pressures which are too high for normal function and may result in irreversible loss of visual function. If untreated, glaucoma may eventually lead to blindness. Ocular hypertension, i.e. the condition of elevated intraocular pressure without optic nerve head damage or characteristic glaucomatous visual field defects, is now believed by many ophthalmologists to represent the earliest phase of glaucoma.

Many of the drugs formerly used to treat glaucoma proved not entirely satisfactory. Topical administration to the eye of agents such as pilocarpine may be used in order to improve the outflow of aqueous humour and reduce the intraocular pressure (see Drugs, 1979, vol 17, 38 and Drugs and Ther. Bull., 1989, vol 21, 85), but these have associated side effects such as emesis and myosis.

We have now found compounds which lower the intraocular pressure without exhibiting side effects to the extent associated with hitherto-known drugs used against glaucoma which act through cholinergic mechanisms.

European patent specifications nos. EP-A-239309, EP-A-301729, EP-A-307142, EP-A-307140, EP-A-323864 and EP-A-322034 describe classes of compounds useful in the treatment of certain neurological and mental illnesses such as Alzheimer's disease. These classes include compounds which are an oxadiazole or thiadiazole, or a salt or prodrug thereof, which is substituted on one of the ring carbon atoms with a non-aromatic azacyclic or azabicyclic ring and substituted on the other ring carbon atom with a substituent of low lipophilicity or a hydrocarbon substituent. We have found that a subclass of these compounds effects reduction of intraocular pressure without exhibiting severe adverse effects on pupil size.

The compounds for use according to the present invention may be represented by structural formula (I):

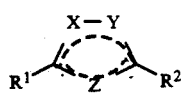

or a salt or prodrug thereof; wherein
one of X, Y, or Z is an oxygen or sulphur atom and the other two are nitrogen atoms, and the dotted circle represents two double bonds thus forming a 1,3,4-oxadiazole, 1,2,4-oxadiazole, 1,3,4-thiadiazole or 1,2,4-thiadiazole nucleus;
$R^1$ represents a non-aromatic azacyclic or azabicyclic ring system selected from

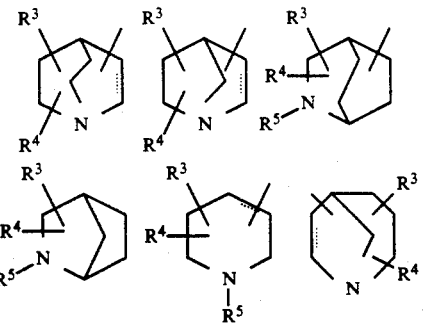

wherein the broken line represents an optional chemical bond;
the substituents $R^3$ and $R^4$ may be present at any position, including the point of attachment to the oxa- or thia-diazole ring, and independently represent hydrogen, $C_{1-4}$ alkyl, halo, $C_{1-4}$ alkoxy, hydroxy or carboxy, or $R^3$ and $R^4$ together represent carbonyl;
the group $R^5$ represents hydrogen or $C_{1-4}$ alkyl; and $R^2$ represents hydrogen, $C_{1-8}$ alkyl optionally substituted by hydroxy or fluoro, $C_{2-8}$ alkenyl, $OR^7$, $SR^7$, $NR^7R^8$, CN, $CO_2R^7$, $CONR^7R^8$ OR $NHCONHR^9$ where $R^9$ is $C_{1-4}$ alkyl; wherein $R^7$ and $R^8$ independently represent hydrogen or saturated or unsaturated $C_{1-8}$ alkyl provided that, when $R_7$ and $R_8$ in $NR^7R^8$ are both hydrogen, at least one of $R^3$ and $R^4$ is $C_{1-4}$ alkyl.

In the definition of $R^1$, it will be appreciated that the nitrogen atom in the azacyclic or azabicyclic ring system will carry a lone pair of electrons.

In the definition of $R^2$, unless otherwise specified, "alkyl" and "alkenyl" groups may be straight, branched or cyclic groups.

One subclass of compounds within the scope of the present invention is represented by formula (II):

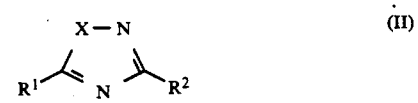

wherein $R^1$, $R^2$ and X are as defined above, and salts and prodrugs thereof.

Preferably, $R^1$ is 1,2,5,6-tetrahydropyridyl (optionally substituted on the ring nitrogen with methyl or ethyl), 1-azabicyclo[2.2.1]heptanyl or 2-azabicyclo[2.2.2]octanyl (isoquinuclidinyl). Also preferred is quinuclidinyl.

Preferably, $R^3$ and $R^4$ are selected from hydrogen, hydroxy and $C_{1-4}$alkyl groups. Especially preferred is when $R^3$ is hydrogen or methyl and $R^4$ is hydrogen.

Preferably, the group $R^5$ represents hydrogen, methyl or ethyl.

Preferably, $R^2$ is $C_{1-8}$ alkyl, more preferably $C_{1-3}$ alkyl, optionally substituted by OH or F, or $NR^7R^8$ when $R^7$ is hydrogen, or saturated or unsaturated $C_{1-3}$ alkyl, and $R^8$ is saturated or unsaturated $C_{1-3}$ alkyl. Especially preferred is when $R^2$ is methyl, ethyl, cyclopropyl, methylamino, dimethylamino or dipropargylamino ($-N(CH_2C\equiv CH)_2$).

Another subclass of compounds within the scope of the present invention is represented by formula (III):

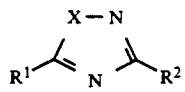

(III)

or a salt or prodrug thereof, wherein $R^1$ is 1,2,5,6-tetrahydropyridyl (optionally substituted on the ring nitrogen with methyl or ethyl), 1-azabicyclo [2.2.1]heptanyl, 2-azabicyclo[2.2.2]octanyl (isoquinuclidinyl), quinuclidinyl or piperidyl;

$R^3$ and $R^4$ are selected from hydrogen, hydroxy and $C_{1-4}$ alkyl (preferred is when $R^3$ is hydrogen);

$R^5$ is hydrogen, methyl or ethyl;

$R^2$ is $C_{1-8}$ alkyl, preferably $C_{1-5}$ alkyl, optionally substituted by OH or F, $C_{2-8}$ alkenyl, preferably ethenyl, $NR^7R^8$ or $CONR^7R^8$ when $R^7$ is hydrogen, or saturated or unsaturated $C_{1-3}$ alkyl, and $R^8$ is hydrogen or saturated or unsaturated $C_{1-3}$ alkyl, or $NHCONHR^9$ where $R^9$ is as defined above. Especially preferred is when $R^2$ is methyl, ethyl, isopropyl, cyclopropyl, n- or sec- pentyl, ethenyl, methylamino, dimethylamino, dipropargylamino, $CONH_2$ or NHCONH(tert-butyl).

Prodrugs of compounds of this invention have a substituent on the oxa- or thia-diazole ring which is convertible in vivo to a substituent as defined for $R^2$, such as a group hydrolysable in vivo to an amino group.

Groups which are hydrolysable in vivo to an amino group on the compounds of this invention may be readily ascertained by administering the compound to a human or animal and detecting, by conventional analytical techniques, the presence of the corresponding compound having an amino substituent in the urine of a human or animal. Examples of such groups include, for example, amido and urethane substituents, in particular a group of formula —NH.Q, wherein Q represents CHO, COR or $CO_2R$, and R represents an optionally substituted hydrocarbon group.

In this context, the hydrocarbon group R includes groups having up to 20 carbon atoms, suitably up to 10 carbon atoms, conveniently up to 6 carbon atoms. Suitable groups R include $C_{1-9}$ alkyl, $C_{2-6}$ alkenyl, $C_{2-6}$ alkynyl, $C_{3-7}$ cycloalkyl, $C_{3-7}$ cycloalkyl($C_{1-6}$)alkyl, aryl, and aryl($C_{1-6}$)alkyl. The alkyl group R may be straight or branched chain and may contain, for example, up to 12 carbon atoms, suitably from 1 to 6 carbon atoms. In particular the group may be substituted methyl, ethyl, n- or iso-propyl, n-, sec-, iso- or tert-butyl, n- or iso-heptyl, or n- or iso-octyl. Suitable cycloalkyl groups include cyclopentyl and cyclohexyl. The aryl group R includes phenyl and naphthyl optionally substituted with up to five, preferably up to three, substituent groups.

Most of the compounds of this invention have at least one asymmetric centre and often more than one; and can therefore exist as both enantiomers and diastereoisomers. In particular, those compounds possessing an unsymmetrical azabicyclic ring system may exist as exo and endo diastereoisomers. It is to be understood that the invention covers all such isomers and mixtures thereof.

Also included within the scope of the present invention are salts of the novel compounds. It will be appreciated that salts of the compounds for use in medicine will be non-toxic pharmaceutically acceptable salts. Other salts may, however, be useful in the preparation of the compounds of the invention or their non-toxic pharmaceutically acceptable salts. Acid addition salts, for example, may be formed by mixing a solution of the compound with a solution of a pharmaceutically acceptable non-toxic acid such as hydrochloric acid, fumaric acid, oxalic, maleic acid, succinic acid, acetic acid, citric acid, tartaric acid, p-toluene sulphonic, carbonic acid or phosphoric acid. Preferred are the hydrochloride, hydrogen oxalate, maleate, tartrate and tosylate salts. Where the novel compound carries a carboxylic acid group the invention also contemplates salts thereof, preferably non-toxic pharmaceutically acceptable salts thereof, such as the sodium, potassium and calcium salts thereof.

Salts of amine groups may also comprise the quaternary ammonium salts in which the amino nitrogen atom carries an alkyl, alkenyl, alkynyl or aralkyl group. Such quaternary ammonium derivatives penetrate poorly into the central nervous system and are therefore useful as peripherally selective muscarinic agents, useful for example as antispasmodic agents, agents to reduce gastric acid secretion, agents to block the muscarinic actions of acetylcholinesterase inhibitors in the treatment of myasthenia gravis and as agents to co-administer with muscarinic agonists in Alzheimer's disease.

Examples of compounds for use according to this invention include:

3-(3-dimethylamino-1,2,4-oxadiazol-5-yl)-5-methyl-1,2,5,6-tetrahydropyridine;

Exo-3-(3-dimethylamino-1,2,4-oxadiazol-5-yl)-1-azabicyclo-[2.2.1]heptane;

3-(3-methylamino-1,2,4-oxadiazol-5-yl)-1,2,5,6-tetrahydropyridine;

3-(3-dimethylamino-1,2,4-oxadiazol-5-yl)-1,2,5,6-tetrahydropyridine:

3-(3-dimethylamino-1,2,4-oxadiazol-5-yl)-1-methyl-1,2,5,6-tetrahydropyridine;

3-(3-dipropargylamino-1,2,4-oxadiazol-5-yl)-1,2,5,6-tetrahydropyridine;

3-(3-methyl-1,2,4-oxadiazol-5-yl)-1-ethyl-1,2,5,6-tetrahydropyridine;

3-(3-cyclopropyl-1,2,4-oxadiazol-5-yl)-1,2,5,6-tetrahydropyridine;

Exo-3-(3-cyclopropyl-1,2,4-oxadiazol-5-yl)-1-azabicyclo[2.2.1]heptane;

Anti-6-(3-ethyl-1,2,4-oxadiazol-5-yl)-2-azabicyclo[2.2.2]octane;

(−)-Anti-6-(3-ethyl-1,2,4-oxadiazol-5-yl)2-azabicyclo[2.2.2]octane;

Endo-3-(3-cyclopropyl-1,2,4-thiadiazol-5-yl)-1-azabicyclo[2.2.1]heptane;

Endo-3-(3-dimethylamino-1,2,4-thiadiazol-5-yl)-1-azabicyclo[2.2.1]heptane; and (3R,4R)-3-(3-cyclopropyl-1,2,4-oxadiazol-5-yl)-1-azabicyclo[2.2.1]heptane;

3-(3-dimethylamino-1,2,4-oxadiazol-5-yl)-1,5-dimethyl-1,2,5,6-tetrahydropyridine;

3-(3-ethyl-1,2,4-oxadiazol-5-yl)-1,5-dimethyl-1,2,5,6-tetrahydropyridine;

3-(3-methyl-1,2,4-oxadiazol-5-yl)-5-methyl-1,2,5,6-tetrahydropyridine;

3-(3-methyl-1,2,4-oxadiazol-5-yl)-1,5-dimethyl-1,2,5,6-tetrahydropyridine;

Exo-3-(3-cyclopropyl-1,2,4-oxadiazol-5-yl)-endo-5-hydroxy-1-azabicyclo[2.2.1]heptane;

Exo-3-(3-dimethylamino-1,2,4-thiadiazol-5-yl)-endo-5-hydroxy-1-azabicyclo[2.2.1]heptane;

Exo-3-(3-isopropyl-1,2,4-thiadiazol-5-yl)-endo-5-hydroxy-1-azabicyclo[2.2.1]heptane;

3-(3-carboxamido-1,2,4-oxadiazol-5-yl)quinuclidine;
Exo-3-(3-isopropyl-1,2,4-oxadiazol-5-yl)-1-azabicy-clo[2.2.1]heptane;
3-(3-ethenyl-1,2,4-oxadiazol-5-yl)-1,2,5,6-tetrahy-dropyridine;
3-(3-ethyl-1,2,4-oxadiazol-5-yl)piperidine;
3-(3-t-butylaminocarbonylamino-1,2,4-oxadiazol-5-yl)quinuclidine;
3-(3-ethyl-1,2,4-oxadiazol-5-yl)quinuclidine;
Exo-3-(3-n-pentyl-1,2,4-oxadiazol-5-yl)-1-azabicy-clo2.2.1]heptane;
Exo-3-(3-(3-methylbut-1-yl)-1,2,4-oxadiazol-5-yl)-1-azabicyclo[2.2.1]heptane;
and salts and prodrugs thereof.

Some of the compounds having the use according to this invention are novel and therefore the present invention further provides:
Exo-3-(3-dimethylamino-1,2,4-oxadiazol-5-yl)-1-azabicyclo-[2.2.1]heptane;
3-(3-methylamino-1,2,4-oxadiazol-5-yl)-1,2,5,6-tetrahy-dropyridine;
3-(3-dimethylamino-1,2,4-oxadiazol-5-yl)-1,2,5,6-tet-rahydropyridine;
3-(3-dimethylamino-1,2,4-oxadiazol-5-yl)-1-methyl-1,2,5,6-tetrahydropyridine;
3-(3-dipropargylamino-1,2,4-oxadiazol-5-yl)-1,2,5,6-tet-rahydropyridine;
3-(3-methyl-1,2,4-oxadiazol-5-yl)-1-ethyl-1,2,5,6-tet-rahydropyridine;
Anti-6-(3-ethyl-1,2,4-oxadiazol-5-yl)2-azabicyclo2.2.-2]octane;
(—)-Anti-6-(3-ethyl-1,2,4-oxadiazol-5-yl)-2-azabicy-clo2.2.2]octane;
3-(3-ethenyl-1,2,4-oxadiazol-5-yl)-1,2,5,6-tetrahy-dropyridine;
3-(3-ethyl-1,2,4-oxadiazol-5-yl)piperidine;
3-(3-t-butylaminocarbonylamino-1,2,4-oxadiazol-5-yl)quinuclidine;
3-(3-ethyl-1,2,4-oxadiazol-5-yl)quinuclidine hydrogen;
Exo-3-(3-n-pentyl-1,2,4-oxadiazol-5-yl)-1-azabicy-clo[2.2.1]heptane;
Exo-3-(3-(3-methylbut-1-yl)-1,2,4-oxadiazol-5-yl)-1-azabicyclo[2.2.1]heptane;
and salts and prodrugs thereof.

The compounds for use according to this invention including the novel compounds of the invention may be prepared as described in the processes (A) to (J) below or by processes analogous to those known to persons skilled in the art.

According to one general process (A) the compounds of this invention having an oxadiazole nucleus may be prepared by a process which comprises reacting a reactive derivative of a carboxylic acid of formula $R^a$—$CO_2H$, with either a compound of formula (IVA) or (IVB) or a salt thereof:

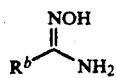
(IVA)

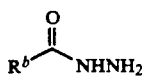
(IVB)

wherein one of $R^a$ and $R^b$ is $R^1$, and the other is $R^2$.

Suitable reactive derivatives of the acid $R^a$—$CO_2H$ include esters, for example $C_{1-4}$ alkyl esters, thio esters, for example pyridylthioester, acid anhydrides, for example $(R^aCO)_2O$, acid halides, for example the acid chloride, orthoesters, and primary, secondary and tertiary amides.

When the compound of formula (IVA) is employed the product of the reaction is a 1,2,4-oxadiazole. It will be appreciated that the compound (IVA) can also be considered as the alternative tautomeric form:

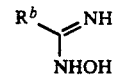

A 3-substituted-1,2,4-oxadiazole-5-yl compound is produced if $R^a$ represents $R^1$ and $R^b$ in formula (IVA) represents $R^2$. In this case, a preferred reactive derivative of the acid $R^a$—$CO_2H$ is a $C_{1-4}$ alkyl ester. The reaction is conveniently carried out in tetrahydrofuran, dimethylformamide or a lower alkanol such as ethanol, propanol or isopropanol at about 20° C. to 100° C. for about 1 to 6 hours.

A 5-substituted-1,2,4-oxadiazol-3-yl compound is produced by the process of this invention when $R^a$ represents $R^2$ and $R^b$ represents $R^1$. For this reaction a suitable reactive derivative is the acid chloride or the acid anhydride $(R^aCO)_2O$. The reaction may be carried out by treating compound (IVA), in the cold, e.g. from about $-5°$ to $+10°$ C., with the reactive derivative, followed by heating at about 80° C.-120° C. for about 1 to 6 hours.

When the compound of formula (IVB) is employed, the product of the process of this invention is a 1,3,4-oxadiazole. In this case, a preferred reactive derivative of the acid $R^aCO_2H$ is an orthoester of formula $R^aC(OR')_3$ where R' represents $C_{1-3}$ alkyl. The process is conveniently effected by heating the hydrazide (IVB) with the orthoester in a solvent such as methanol at reflux temperature for about 2 to 8 hours. An intermediate of formula: $R^b.CO.NH.N=C(Ra)OR'$, may be isolated by evaporation of the solvent. The intermediate is then treated with a strong base such as potassium t-butoxide or 1,8-diazabicyclo[5.4.0]undec-7-ene, in butanol for about 10 to 24 hours at about 90°-150° C.

The compounds of this invention having an oxadiazole nucleus may also be prepared by:
(B) reacting a compound of formula $R^a$—CO—N=C($R^b$)N($CH_3$)$_2$, with hydroxylamine;
(C) oxidizing an oxadiazoline with an oxidizing agent such as potassium permanganate, nitrogen dioxide, or N-bromosuccinimide; or
(D) when $R^2$ is amino, reacting a compound of formula (IVA) with a cyanogen halide, such as cyanogen bromide.

The compounds of this invention having an thiadiazole nucleus may be prepared by:
(E) (for the preparation of 1,2,4-thiadiazoles), cyclisation of a compound of formula:

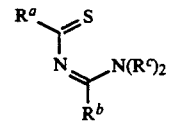

wherein one of $R^a$ and $R^b$ is a group $R^1$, and the other is a group $R^2$; and $R^c$ is hydrogen or an alkyl group.

Cyclisation can be achieved using an aminating agent such as hydroxylamine-O-sulphonic acid in a lower alkanol such as methanol, ethanol or propanol, in the presence of pyridine, at between −20° C. and 50° C. for about 1-6 hours.

When $R^c$ is H, cyclisation may also be achieved by use of an oxidising agent such as bromine, iodine, hydrogen peroxide or nitric acid;

(F) (for the preparation of 1,2,4-thiadiazoles) cycloaddition of a nitrile sulphide $R^a$-C≡N+—S− with a nitrile of formula $R^bCN$ where $R^a$ and $R^b$ are as defined above.

(G) (for the preparation of 1,2,4-thiadiazoles) reaction of a thiadiazole of formula:

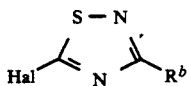

with a reagent which provides as anion $^-R^a$, where $R^a$ and $R^b$ are as previously defined and Hal represents halogen.

Reagents which may provide the anion $^-R^a$ include a Grignard reagent $R^aMgY$ (where Y=halogen); an organocuprate reagent such as $LiR^a_2Cu$; an organolithium reagent $R^aLi$; or a compound which stabilises the anion by means of an adjacent activating group such as an ester or enolisable ketone function. In this case, the adjacent ester or ketone function may be retained after the process is complete, or may be removed. For example, an ester moiety may be hydrolysed and decarboxylated.

(H) (for the preparation of 1,2,5-thiadiazoles) reaction of a diamine of the type

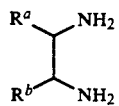

where $R^a$ and $R^b$ are as defined above, with a sulphur chloride such as thionyl chloride or sulphur dichloride.

(J) (for the preparation of 1,3,4-thiadiazoles) dehydration of a thiosemicarbazide of formula $R^xCSNHNHCONR^pR^q$ where $R^x$ is an azacyclic or azabicyclic ring system and $R^p$ and $R^q$ are hydrogen or an alkyl group, with a dehydrating agent such as sulphuric acid, polyphosphoric acid or methanesulphonic acid.

The azacyclic or azabicyclic moiety may be introduced into the molecules concerned by methods known from the art, in particular by methods analogous to those described in EP-A-0239309.

In any of the above reactions it may be necessary and/or desirable to protect any sensitive groups in the compounds. For example, if $R^a$ and/or $R^b$ include amino, carboxy, hydroxy or thiol groups, these may be protected in conventional manner. Thus, suitable protecting groups for hydroxy groups include silyl groups such as trimethylsilyl or t-butyldimethylsilyl, and etherifying groups such as tetrahydropyranyl; and for amino groups include benzyloxycarbonyl and t-butoxycarbonyl. Carboxy groups are preferably protected in a reduced form such as in the form of their corresponding protected alcohols, which may be subsequently oxidised to give the desired carboxy group. Thiol groups may be protected by disulphide formation, either with the thiol itself or with another thiol to form a mixed disulphide. The protecting groups may be removed at any convenient stage in the synthesis of the desired compound according to conventional techniques.

When administered for the treatment of elevated intraocular pressure or glaucoma, the active compound is preferably administered topically to the eye, although systemic treatment is, as indicated, also possible. The dose administered can be from as little as 0.1 to 25 mg or more per day, singly, or preferably on a 2 to 4 dose per day regimen although a single dose per day is satisfactory.

The present invention therefore also provides a pharmaceutical formulation suitable for use in reducing intraocular pressure or for treating glaucoma which formulation comprises a novel compound of formula (I) and a pharmaceutically acceptable carrier.

It will be understood that any formulation may further comprise another active ingredient such as another antiglaucoma agent for example a topical carbonic anhydrase inhibitor.

When given systemically, the drug can be given by any route, although the oral route is preferred. In oral administration, the drug can be employed in any of the usual dosage forms such as tablets or capsules, either in a contemporaneous delivery or sustained release form. Any number of the usual excipients or tabletting aids can likewise be included. Further details of suitable formulations are given in the aforementioned European patent specifications.

When given by the topical route, the active compound or an ophthalmologically acceptable salt thereof such as the hydrochloride salt is formulated into an ophthalmic preparation. In such formulations, from 0.0005% to 15% by weight can be employed. The objective is to administer a dose of from 0.1 to 1.0 mg per eye per day to the patient, with treatment continuing so long as the condition persists.

Thus, in an ophthalmic solution, insert, ointment or suspension for topical delivery, or a tablet, intramuscular or intravenous composition for systemic delivery, the active medicament or an equivalent amount of a salt thereof is employed, the remainder being carrier, excipients, preservatives and the like as are customarily used in such compositions.

The active drugs of this invention are most suitably administered in the form of ophthalmic pharmaceutical compositions adapted for topical administration to the eye such as a suspension, ointment, or as a solid insert. A preferred composition is eye drops. Formulations of these compounds may contain from 0.0005 to 15% and especially 0.05% to 2% of medicament. Higher dosages as, for example, about 10% or lower dosages can be employed provided the dose is effective in reducing or controlling elevated intraocular pressure. As a unit dosage from between 0.001 to 10.0 mg, preferably 0.005 to 2.0 mg, and especially 0.1 to 1.0 mg of the compound is generically applied to the human eye, generally on a daily basis in single or divided doses so long as the condition being treated exists.

This invention therefore further provides a pharmaceutical formulation adapted for topical administration to the eye which formulation comprises a compound of formula (I) and a carrier suitable for topical administration.

These hereinbefore described dosage values are believed accurate for human patients and are based on the known and presently understood pharmacology of the compounds, and the action of other similar entities in the human eye. As with all medications, dosage requirements are variable and must be individualized on the basis of the disease and the response of the patient.

For topical administration, pharmaceutically acceptable carriers are, for example, water, mixtures of water and water-miscible solvents such as lower alkanols or arylalkanols, vegetable oils, polyalkylene glycols, petroleum based jelly, ethyl cellulose, ethyl oleate, carboxymethylcellulose, polyvinylpyrrolidone, isopropyl myristate and other conventionally-employed non-toxic, pharmaceutically acceptable organic and inorganic carriers. The pharmaceutical preparation may also contain non-toxic auxiliary substances such as emulsifying, preserving, wetting agents, bodying agents and the like, as for example, polyethylene glycols 200, 300, 400 and 600, carbowaxes 1,000, 1,500, 4,000, 6,000 and 10,000, antibacterial components such as quaternary ammonium compounds, phenylmercuric salts known to have cold sterilizing properties and which are non-injurious in use, thimerosal, methyl and propyl paraben, benzyl alcohol, phenyl ethanol, buffering ingredients such as sodium chloride, sodium borate, sodium acetates, gluconate buffers, and other conventional ingredients such as sorbitan monolaurate, triethanolamine, oleate, polyoxyethylene sorbitan monopalmitylate, dioctyl sodium sulfosuccinate, monothioglycerol, thiosorbitol, ethylenediamine tetraacetic acid, and the like. Additionally, suitable ophthalmic vehicles can be used as carrier media for the present purpose including conventional phosphate buffer vehicle systems, isotonic boric acid vehicles, isotonic sodium chloride vehicles, isotonic sodium borate vehicles and the like.

The pharmaceutical formulation may also be in the form of a solid insert such as one which after dispensing the drug remains essentially intact, or a bioerodible insert that is soluble in lacrimal fluids or otherwise disintegrates.

The present invention will now be illustrated by the following descriptions and examples:

DESCRIPTIONS

The following descriptions exemplify the preparation of compounds having the use according to the present invention:

Description A: 3-(3-Dimethylamino-1,2,4-oxadiazol-5-yl)-5-methyl-1,2,5,6-tetrahydrdoyridine hydrochloride Prepared according to Example 3 of European patent specification no. 322 034.

Description B: 3-(3-Cyclopropyl-1,2,4-oxadiazol-5-yl)-1,2,5,6-tetrahydropyridine hydrochloride Prepared according to Example 6 of European patent specification no. 323 864.

Description C: Exo-3-(3-Cyclopropyl-1,2,4-oxadiazol-5-yl)-1-azabicyclo-[2.2.1]heptane hydrochloride Prepared according to Example 5 of European patent specification no. 323 864.

Description D: Endo-3-(3-Cyclopropyl-1,2,4-thiadiazol-5-yl)-1-azabicyclo[2.2.1]heptane hydrogen oxalate Prepared according to Example 14 of European patent specification no. 307 142.

Description E: Endo-3-(3-Dimethylamino-1,2,4-thiadiazol-5-yl)-1-azabicyclo[2.2.1]heptane hydrogen oxalate Prepared according to Example 11 of European patent specification no. 307 142.

Description F: 3-(3-Dimethylamino-1,2,4-oxadiazol-5-yl)-1,5-dimethyl-1,2,5,6-tetrahydropyridine sesquioxalate Prepared according to Example 6 of European Patent specification No. 322 034.

Description G: 3-(3-Ethyl-1,2,4-oxadiazol-5-yl)-1,5-dimethyl-1,2,5,6-tetrahydropyridine hydrogen oxalate Prepared according to Example 5 of European Patent specification No.322 034.

Description H: 3-(3-Methyl-1,2,4-oxadiazol-5-yl)-5-methyl-1,2,5,6-tetrahydropyridine hydrochloride Prepared according to Example 1 of European Patent specification No. 322 034.

Description I: 3-(3-Methyl-1,2,4-oxadiazol-5-yl)-1,5-dimethyl-1,2,5,6-tetrahydropyridine hydrogen oxalate Prepared according to Example 4 of European Patent specification No. 322 034.

Description J: Exo-3-(3-Cyclopropyl-1,2,4-oxadiazol-5-yl)-endo-5-hydroxy-1-azabicyclo[2.2.1]heptane hydrogen oxalate Prepared according to Example 20 of European Patent specification No. 323 864.

Description K: Exo-3-(3-Dimethylamino-1,2,4-thiadiazol-5-yl)-endo-5-hydroxy-1-azabicyclo[2.2.1-]heptane oxalate Prepared according to Example 33 of European Patent specification No. 307 142.

Description L: Exo-3-(3-Isopropyl-1,2,4-thiadiazol-5-yl)-endo-5-hydroxy-1-azabicyclo[2.2.1]heptane hydrogen oxalate Prepared according to Example 42 of European Patent specification No. 307 142.

Description M: 3-(3-Carboxamido-1,2,4-oxadiazol-5-yl)quinuclidine hydrochloride

Prepared according to the procedure described in *J. Med. Chem.*, 1990, 33, 1128–1138.

Description N: Exo-3-(3-Isopropyl-1,2,4-oxadiazol-5-yl)-1-azabicyclo[2.2.1]heptane hydrochloride Prepared according to Example 25 of European Patent specification No. 323 864.

EXAMPLE 1

(3R,4R)-3-(3-Cyclopropyl-1,2,4-oxadiazol-5-yl)-1-azabicyclo[2.2.1]heptane. Hydrochloride (3S,4R)-Ethyl-1-azabicyclo[2.2.1]heptane-3-carboxylate hydrogen oxalate (61.7 g, 0.24 mol) in $H_2O$ (200 mL) was cooled in an ice bath, $Na_2CO_3$ (38 g, 0.36 mol) added and the mixture extracted with $CH_2Cl_2$ (5×250 mL). The combined organics were dried ($Na_2SO_4$) and evaporated to give the free base as a colourless oil (38.2 g, 94%). To a stirred solution of cyclopropyl carboxamide oxime (22.6 g, 0.226 mol) in dry THF (500 mL) was added 4A molecular sieves (40 g). After 0.5h, NaH (9.9 g, of a 55% dispersion in oil, 0.226 mol) was added under nitrogen atmosphere in portions over 40 min. After addition was complete, the mixture was heated at 50° C. (oil bath temperature) for 1h. A solution of the ester free base (19.1 g, 0.113 mol, obtained above) in dry THF (200 mL) was added and the mixture heated under reflux for 3h. After cooling, $H_2O$ (100 mL) was added and the mixture stirred for a further 15 min before filtering. The filtrate was evaporated in vacuo to remove most of the THF and the crude product was extracted into $CH_2Cl_2$ (5×250 mL). The combined organics were dried ($Na_2SO_4$) then evaporated to give a yellow oil (25.1 g) which was combined with a similar quantity from an identical reaction (total 49.3 g). Column chromatography on neutral alumina (ICN Neutral Alumina, Grade 3; 2.2 Kg) using $CH_2Cl_2/MeOH$ (100:1) gave pure exo-(3R,4R) product as a pale yellow oil (18.05 g, $R_t$ 10.12 min (>99%), BP10 Capillary GC column, 170° C. isothermal). Mixed fractions were also obtained (~1:1 exo/endo, 13.25 g) and this material was re-equilibrated under thermodynamic conditions using NaOMe (4.8 g; 1.5 equivalents) in MeOH (100 mL) at reflux for 2h. The mixture was evaporated and partitioned between $H_2O$ (40 mL) and $CH_2Cl_2$ (100 mL). The organic layer was separated and the aqueous re-extracted with $CH_2Cl_2$ (2×100 mL). The combined organic extracts were dried and evaporated to give a pale yellow oil (13.0 g; ~5:1, exo/endo) to afford a further supply of pure exo isomer (7.8 g) after column chromatography on neutral alumina (total yield, 25.85 g). This material in $Et_2O$ (180 mL) containing iPA (18 mL) was filtered and cooled (ice bath) and then treated with saturated etherial HCl. After ageing for 0.5h at 5° C., the crude salt was collected (24.4 g) and recrystallised twice from iPA (60 mL each time) to afford the title compound as a white crystalline solid (18.0 g; 31%), m.p. 169°-170° C.; (Found: C, 54.65; H, 6.67; N, 17.32; Cl, 14.76. $C_{11}H_{15}N_3O \cdot HCl$ requires C, 54.66; H, 6.67; N, 17.38; Cl, 14.67%); $R_f$ 0.62 in $CH_2Cl_2/MeOH$ (50:1) on alumina plates; $[\alpha]_D^{22°\ C.}$ −0.30° (c=1.0, MeOH); $[\alpha]_D^{22°\ C.}$ −17.4° (c=1.0, $CH_2Cl_2$); HPLC, chemical purity: $R_t$ 6.56 min (99.9%) at $\lambda$=210 nm on a Spherisorb ODS2 column (250×4.6 mm), 10% MeCN in 50 mM $KH_2PO_4$, 0.2% TEA, pH=2.5 with $H_3PO_4$, flow rate 1 mL/min; HPLC, enantiomeric purity: $R_t$ 7.06 min (>99%) at $\lambda$=205 nm on an Enantiopac column, 5 mM $K_2HPO_4$, 0.5 mM t-butyldihydrogen ammonium phosphate, pH=7.5 with $H_3PO_4$, flow rate 0.3 mL/min; MS, m/z 205 M+ of free base; IR $\lambda_{max}$ (nujol) 2800-2400 (NH+), 1580 cm$^{-1}$ (C=N); $^1$N NMR (360 MHz, $D_2O$) δ 0.95-1.02 (2H, m, cyclopropyl-$CH_2$), 1.11-1.21 (2H, m, cyclopropyl-$CH_2$), 1.96-2.05 (1H, m, 5-CH). 2.08-2.16 (1H, m, cyclopropyl-CH), 2.23-2.33 (1H, m5-CH), 3.30-3.46 (4H, m, 4-CH, 6-CH, 7-$CH_2^l$), 3.50-3.60 (1H, m, 6-CH) and 3.71-3.87 (3H, m, 2-$CH_2$ and 3-CH).

EXAMPLE 2

Exo 3-(3-Dimethylamino-1,2,4-oxadiazol-5-yl)-1-azabicyclo[2.2.1]heptane Hydrochloride N,N, Dimethyl-hydroxyguandine hydrochloride (1.04 g, 0.0074 mol) and 4A molecular sieves (5 g) were stirred in anhydrous tetrahydrofuran (40 mL) under a nitrogen atmosphere for 0.5 hour. Sodium hydride (0.34 g of an 80% oil dispersion, 0.012 mol) was added and after the initial evolution of hydrogen the mixture was stirred at 75° C. for 1.5 hours. Exo Methyl-1-azabicyclo[2.2.1]heptane3-carboxylate (0.46 g, 0.003 mol, J.C.S. Chem. Commun., 1988, 1618) in a minimum volume of anhydrous tetrahydrofuran was added and the mixture stirred with heating under reflux for 3 hours. The mixture was poured into water (15 mL) and dichloromethane (50 mL) was added. The organic layer was separated and the aqueous re-extracted with dichloromethane.

The combined organics were dried (sodium sulphate), filtered, then evaporated to give a yellow oil (0.39 g) which was purified by column chromatography on silica by elution with dichlormethane/methanol (93:7) to yield the title compound free base as an oil.

The hydrochloride salt had mp 164°-168° C. (propan-2-ol/diethyl ether). Mass Spectrum, m/z 208 for M+ (of free base); $^1$H NMR (360 MHz, $D_2O$) δ 1.95-2.02 (1H, m) and 2.22-2.32 (1H, m, 5-$CH_2$); 2.98 (6H, s, 2×$CH_3$); 3.29-3.78 (7H, m, 2-$CH_2$, 4-CH, 6-$CH_2$ and 7-$CH_2$); 3.83-3.89 (1H, m, 3-CH). (Found: C, 48.31; H, 6.96; N, 22.76. $C_{10}H_{16}H_4O \cdot HCl$ 0.2$H_2O$ requires C, 48.37; H, 7.06; N, 22.56%).

EXAMPLE 3

3-(3-Methylamino-1,2,4-oxadiazol-5-yl)-1,2,5,6-tetrahydropyridine Hydrochloride a)

1-t-Butyloxycarbonyl-3-(3-methylamino-1,2,4-oxadiazol-5-yl)-1,2,5,6-tetrahydropyridine N-Methyl-hydroxyguanidine sulphate (17.0 g, 0.061 mol) was stirred with 4A molecular sieves (20 g) in ethanol (80 mL) under a nitrogen atmosphere for 2 hours. Sodium (2.8 g, 0.122 mol) was added in portions then the mixture was stirred at 50° C. for 1 hour. A solution of methyl 1-t-butyloxycarbonyl-1,2,5,6-tetrahydropyridine-3-carboxylate (3.0 g, 0.012 mol) in ethanol (40 mL) was added and the reaction mixture was stirred whilst heating under reflux for 4 hours. The mixture was cooled, filtered, evaporated to dryness. The residue was dissolved in tetrahydrofuran (40 mL), treated with potassium t-butoxide (1.35 g, 0.012 mol) and stirred for 3 hours. Water (50 mL) was added and the mixture extracted with dichloromethane (5×50 mL). The combined organics were dried (sodium sulphate) then evaporated to dryness to give a yellow gum which was purified by column chromatography on silica using dichloromethane/methanol (80:1) afford the product as a pale yellow gum (1.10 g, 33%). (HRMS, Found: M+, 280.1530, $C_{13}H_{20}N_4O_3$ requires M, 280.1535). (Found: C, 54.70; H, 7.29; N, 18.91. $C_{13}H_{20}N_4O_3$ requires C, 55.70; H, 7.19, N, 19.99%).

b)

3-(3-Methylamino-1-2,4-oxadiazol-5-yl)-1,2,5,6-tetrahydropyridine Hydrochloride The foregoing oxadiazole (1.05 g, 0.0037 mol) was stirred with trifluoracetic acid (1.7 mL, 0.022 mol) in dichloromethane (10 mL) for 18 hours.

The hydrochloride salt had mp 231°-233° C. (propan-2-ol/methanol). Rf=0.56 in dichloromethane/methanol (9:1) on alumina plates. Mass Spectrum, m/z 179 for (M−H)+ of free base; IR (nujol) $\lambda_{max}$ 3310 (NH), 2800-2500 (NH+), 1665 cm$^{-1}$ (C=C, C=N); $^1$H NMR (360 MHz, $D_2O$) δ 2.70-2.75 (2H, m, 5-$CH_2$); 2.84 (3H, s, $CH_3$); 3.45 (2H, dd, J=6 Hz, 6-$CH_2$); 4.10 (2H, dd, J=2 Hz, 2-$CH_2$); 7.23-7.25 (1H, m, 4-CH). Found: C, 44.34; H, 6.16; N, 25.30. $C_8H_{12}N_4O \cdot HCl$ requires C, 44.35; H, 6.05; N, 25.86%).

EXAMPLE 4

3-(3-Dimethylamino-1,2,4-oxadiazol-5-yl)-1,2,5,6-tetrahydropyridine Hydrochloride N,N-Dimethyl-hydroxyguanidine hydrochloride (7.40 g, 0.053 mol) was stirred with 4A molecular sieves (25 g) in anhydrous tetrahydrofuran (150 mL) for 0.5 hour under a nitrogen atmosphere. Sodium hydride (4.8 g of a 55% oil dispersion, 0.11 mol) was added in portions then the mixture was heated at 50° C. for 1 hour.

A solution of 3-methoxycarbonyl-1-vinyloxycarbonyl-1,2,5,6-tetrahydrofuran (50 mL) was added and the mixture stirred whilst heating under reflux for 2 hours. The mixture was cooled, water (100 mL) and dichloromethane (250 mL) were added then filtered. The organic layer was separated and the aqueous re-extracted with dichloromethane (100 mL). The combined organics were dried (sodium sulphate) then evaporated to give an orange oil (6.20 g). The product was purified by column chromatography on neutral alumina (Grade 3) using dichloromethane/methanol (120:1) to afford the title compound free base as a yellow oil (3.15 g, 68%). The hydrochloride salt had mp 200°–201° C. (propan-2-ol). Rf=0.78 in dichloromethane/methanol (9:1) on alumina plates. Mass Spectrum, m/z 194 for M+ of free base; IR (nujol) $\lambda_{max}$ 2800–2300 (NH+), 1665 cm$^{-1}$ (C=C, C=N); $^1$H NMR (360 MHz, D$_2$O) δ 2.70–2.76 (2H, m, 5-CH$_2$); 3.00 (6H, s, 2×CH$_3$); 3.46 (2H, dd, J=6 Hz, 6-CH$_2$); 4.11–4.14 (2H, m, 2-CH$_2$); 7.23–7.27 (1H, m, 4-CH). (Found: C, 46.85; H, 6.57; N, 24.15. C$_9$H$_{14}$N$_4$O. HCl requires C, 46.86; H, 6.55 N, 24.29%).

EXAMPLE 5

3-(3-Dimethylamino-1,2,4-oxadiazol-5-yl)-1-methyl-1,2,5,6-tetrahydropyridine Hydrochloride The title compound free base (1.50 g, 55%) was obtained from arecoline (2.0 g, 0.013 mol) and N,N-Dimethylhydroxyguanidine hydrochloride (3.63 g, 0.026 mol) in a similar manner as described for Example 4. The hydrochloride salt had mp 202°–203° C. (propan-2-ol/methanol). (Found: C, 48.92; H, 6.94; N, 22.75. C$_{10}$H$_{16}$N$_4$O. HCl requires C, 49.08; H, 7.00; N, 22.89%).

EXAMPLE 6

3-(3-Dipropargylamino-1,2,4-oxadiazol-5-yl)-1,2,5,6-tetrahydropyridine Hydrogen Oxalate a)

1-t-Butyloxycarbonyl-3-(3-amino-1,2,4-oxadiazol-5-yl)-1,2,5,6-tetrahydropyridine The title compound (1.72 g, 16%) was prepared from hydroxyguanidine hemisulphate hemihydrate (55.90 g, 0.42 mol) and methyl 1-t-butyloxycarbonyl-1,2,5,6-tetrahydropyridine-3-carboxylate (10.0 g, 0.041 mol). Mass Spectrum, m/z 266 for M+.

b) 1-t-Butyloxycarbonyl-3-(3-dipropargyl amino-1,2,4-oxadiazol-5-yl)-1,2,5,6-tetrahydropyridine Sodium hydride (65 mg of a 55% oil dispersion, 0.0015 mol) was added to a stirred solution of the foregoing amino-oxadiazole (350 mg, 0.0013 mol) in anhydrous tetrahydrofuran (12 mL) under a nitrogen atmosphere. A solution of propargyl bromide (0.11 mL, 0.0015 mol) in anhydrous tetrahydrofuran (3 mL) was added dropwise and the mixture was stirred at room temperature for 72 hours. Water (30 mL) was added and the mixture extracted with dichloromethane (20 mL). The organic layer was separated and the aqueous further extracted with dichloromethane (20 mL). The combined organics were washed with water (20 mL), dried (sodium sulphate) then evaporated to give a gum (480 mg) which was purified by column chromatography on silica using dichloromethane/methanol (100:1) to afford the title compound as a yellow oil (150 mg, 38%). Mass Spectrum, m/z 344 for (M+2H)+; $^1$H NMR (360 MHz, CDCl$_3$) δ 1.49 (9H, s, 3×CH$_3$); 2.26–2.28 (2H, m, 2×C≡CH); 2.34–2.42 (2H, m, 5-CH$_2$); 3.55 (2H, dd, J=6 Hz, 6-CH$_2$); 4.24–4.34 (6H, m, 2-CH$_2$, 2×CH$_2$C≡C); 7.06–7.10 (1H, m, 4-CH).

c) 3-(3-Dipropargylamino-1,2,4-oxadiazol-5-yl)-1,2,5,6-tetrahydropyridine Hydrogen Oxalate The foregoing oxadiazole (135 mg, 0.00039 mol) was stirred with trifluoroacetic acid (0.18 mL, 0.0024 mol) in dichloromethane (6 mL) for 24 hours. The hydrogen oxalate salt had mp 134°–135° C. (propan-2-ol). Rf=0.78 in dichloromethane/methanol (9:1) on alumina plates. Mass Spectrum, m/z 242 for M+ of free base. (Found: C, 53.87; H, 4.90; N, 16.52. C$_{13}$H$_{14}$N$_4$O. C$_2$H$_2$O$_4$ requires C, 54.21; H, 4.85; N, 16.86%).

EXAMPLE 7

1-Ethyl-3-(3-methyl-1,2,4-oxadiazol-5-yl)-1,2,5,6-tetrahydropyridine Hydrochloride a) 3-(3-Methyl-1,2,4-oxadiazol-5-yl)-1,2,5,6-tetrahydropyridine

The title compound (5.20 g, 66%) was obtained from 3-methoxycarbonyl-1-vinyloxycarbonyl-1,2,5,6-tetrahydropyrine (10 g, 0.047 mol) and acetamide oxime (6.95 g, 0.094 mol). Mass Spectrum, m/z 164 for (M−H)+.

b) 1-Ethyl-3-(3-methyl-1,2,4-oxadiazol-5-yl)-1,2,5,6-tetrahydropyridine Hydrochloride Sodium hydride (280 mg of a 55% oil dispersion, 0.0064 mol) was added to a stirred solution of the foregoing oxadiazole (1.05 g, 0.0064 mol) in anhydrous tetrahydrofuran (10 mL) under a nitrogen atmosphere. After 20 minutes a solution of iodoethane (0.51 mL, 0.0064 mol) in anhyydrous tetrahydrofuran (5 mL) was added dropwise. After stirring at room temperature for 8 hours the mixture was filtered then evaporated to dryness in vacuo. The residue was purified by column chromatography on neutral alumina (Grade 3) using dichloromethane/petroleum ether (40–60) (3:1) to afford the title compound free base as a colourless oil (0.51 g, 41%). The hydrochloride salt had mp 157°–158° C. (methanol/diethyl ether). Rf=0.80 in dichloromethane/methanol (9:1) on alumina plates. Mass Spectrum, m/z 192 for (M−H)+ of free base; IR (nujol) $\lambda_{max}$ 2600–2200 (NH+), 1660 cm$^{-1}$ (C=C, C=N); $^1$H NMR (360 MHz, D$_2$O) δ 1.42 (3H, t, J=7 Hz, CH$_2$CH$_3$); 2.42 (3H, s, oxadiazole-CH$_3$); 2.78–2.84 (2H, m, 5-CH$_2$); 3.40 (2H, q, J=7 Hz, CH$_2$CH$_3$); 3.44–3.64 (2H, m, 6-CH$_2$); 4.10–4.30 (2H, m, 2-CH$_2$); 7.30–7.33 (1H, m, 4-CH). (Found: C, 48.76; H, 6.62; N, 16.98. C$_{10}$H$_{15}$N$_3$O. HCl. H$_2$O requires C, 48.49; H, 7.32; N, 16.96%).

EXAMPLE 8

Anti-6-(3-Ethyl-1,2,4-oxadiazol-5-yl)-2-azabicyclo[2.2.2]octane Hydrochloride a) Anti 2-t-Butyloxycarbonyl-6-(3-ethyl-1,2,4-oxadiazol-5-yl)-2-azabicyclo[2.2.2]octane The title compound (0.75 g, 22%) was obtained from propionamide oxime (2.11 g, 0.023 mol) and anti methyl 2-t-butyloxycarbonyl-2-azabicyclo[2.2.2]octane-6-carboxylate (3.0 g, 0.011 mol, EPA 307142)

b) Anti 6-(3-Ethyl-1,2,4-oxadiazol-5-yl)-2-azabicyclo[2.2.2]octane Hydrochloride The foregoing oxadiazole (0.703 g, 0.00229 mol) was stirred with trifluoracetic acid (3.53 mL, 0.046 mol) in dichloromethane (8 mL) for 3 hours. The hydrochloride salt had mp 166°-167° C. (propan-2-ol). Rf=0.33 in dichloromethane/methanol (20:1) on silica plates. Mass Spectrum, m/z 208 for (M+H)+ of free base. (Found: C, 54.27; H, 7.39; N, 17.27. $C_{11}N_{17}N_3O$. HCl requires C, 54.21; H, 7.44; N, 17.24%).

EXAMPLE 9

(−) Anti 6-(3-Ethyl-1,2,4-oxadiazol-5-yl)-2-azabicyclo[2.2.2]octane Hydrochloride (−)-Dibenzoyltartaric acid (4.09 g, 0.114 mol) in ethanol (25 mL) as added to a solution of racemic anti 6-(3-ethyl-1,2,4-oxadiazol-5-yl)-2-azabicyclo[2.2.2]octane (9.47 g, 0.0457 mol, Example 10) in ethanol (15 mL). The crystals were collected and the mother liquors evaporated to dryness then the free base liberated. This free base was treated with (+)-dibenzoyl tartaric acid (3.48 g, 0.0097 mol) in ethanol (35 mL). The crystals were collected and recrystallised once from propan-2-ol then twice from ethanol to afford the (+)-DBT salt as crystalline solid (0.83 g), mp 171°-172° C. The hydrochloride salt had mp 187°-188° C. [α]$_D$22° C.−52.4° (c=1, methanol). Found: C, 53.98; H, 7.41; N, 17.03. $C_{11}H_{17}N_3O$. HCl requires C, 54.21; H, 7.44; N, 17.24%).

EXAMPLE 10

3-(3-Ethenyl-1,2,4-oxadiazol-5-yl)-1,2,5,6-tetrahydropyridine Trifluoroacetate a) 1-t-Butyloxycarbonyl-3-(3-(2-hydroxethyl)-1,2,4-oxadiazol-5-yl)-1,2,5,6-tetrahydropyridine The title compound (8.0 g, 45%) was prepared from 3-hydroxypropionamide oxime (15.90 g, 0.15 mol), methyl 1-t-butyloxycarbonyl-1,2,5,6-tetrahydropyridine-3-carboxylate (14.48 g, 0.06 mol) and sodium (3.45 g, 0.15 mol) in ethanol (550 mL). Mass spectrum, m/z 296 (M+H)+.

b) 1-t-Butyloxycarbonyl-3-(3-(2-methanesulphonyloxyethyl)-1,2,4-oxadiazol-5-yl)-1,2,5,6-tetrahydropyridine The title compound (8.0 g, 93%) was prepared from the foregoing hydroxy compound (6.76 g, 23 mmol), triethylamine (3.33 mL, 24 mmol) and methanesulphonyl chloride (1.8 mL), 23 mmol) in dichloromethane (50 mL). Mass spectrum, CI+, m/z 318 (McLafferty rearrangement ion).

c) 1-t-Butyloxycarbonyl-3-(3-ethenyl-1,2,4-oxadiazol-5-yl)-1,2,5,6-tetrahydropyridine 1,8-Diazabicyclo[5.4.0]undec-7-ene (3.1 mL, 21 mmol) was added to a solution of the foregoing mesylate (7.70 g, 21 mmol) in toluene (30 mL) and heated at 65° C. for 4.5 hours. After cooling water (30 mL) was added, the organic layer separated, dried then evaporated. The crude product was purified by column chromatography on silica using dichloromethane/methanol (200:1) to afford the title compound as a colourless solid (4.44 g, 76%), mp 81°-82° C. Rf 0.58 in ethyl acetate/petroleum ether (60-80) (1:1) on silica plates. Mass spectrum, m/z 221 (McLafferty rearrangement ion).

d) 3-(3Ethenyl-1,2,4-oxadiazol-5-yl)-1,2,5,6-tetrahydropyridine Trifluoroacetate Trifluoroacetic acid (22 mL, 280 mmol) was added to a cooled (4° C.) solution of the foregoing olefin (4.0 g, 14 mmol) in dichloromethane (20 mL). After 2 hours at room temperature the mixture was evaporated to dryness and the title compound recrystallised from propan-2-ol (2.95 g, 72%), mp 92°-94° C. Mass spectrum, m/z 177 for M+ of free base (Found: C, 45.39; H, 4.21; N, 14.30. $C_9H_{11}N_3O$. $CF_3CO_2H$ requires C, 45.37; H, 41.5; N, 14.43%).

EXAMPLE 11

3-(3-Ethyl-1,2,4-oxadiazol-5-yl)piperidine Hydrochloride

The title compound free base (1.25 g, 73%) was obtained from ethyl nipecotate (1.50 g, 9.5 mmol), propionamide oxime (1.26 g, 14.3 mmol) and sodium hydride (0.624 g of a 55% oil dispersion, 14.3 mmol) in anhydrous tetrahydrofuran (85 mL). The hydrochloride salt had mp 120°-121° C. (propan-2-ol/diethyl ether). $R_f$ 0.77 in dichloromethane/methanol (9:1) on alumina plates. Mass spectrum, m/z 182 for (M+H)+ of free base; 1H NMR (360 MHz, $D_2O$) δ 1.28 (3H, t, J=7.5 Hz, $CH_3$); 1.87-2.08 (3H, m) and 2.28-3.55 (1H, m, 4-$CH_2$ and 5-$CH_2$); 2.78 (2H, q, J=7.5 Hz, $CH_2$); 3.08-3.16 (1H, m, one of 6-$CH_2$); 3.39 (1H, dd, J=10, 13 Hz, one of 2-$CH_2$); 3.40-3.47 (1H, m one of 6-$CH_2$); 3.56-3.64 (1H, m, 3-CH); 3.76 (1H, dd, J=4, 13 Hz, one of 2-$CH_2$). (Found: C, 49.54; H, 7.30; N, 19.15. $C_9H_{15}N_3O$.HCl requires C, 49.65; H, 7.41; N, 19.30%).

EXAMPLE 12

3-(3-t-Butylaminocarbonylamino-1,2,4-oxadiazol-5-yl)quinuclidine Hydrochloride The title compound free base (0.58 g, 73%) was prepared using 3-(3-amino-1,2,4-oxadiazol-5-yl)quinuclidine (0.52 g, 2.7 mmol) and t-butylisocyanate (1 mL, 8.7 mmol) in pyridine (10 mL) at 100° C. for 24 hours. The hydrochloride salt had mp 206° C. (methanol/diethyl ether). $R_f$ 0.50 in dichloromethanemethanol (20:1) on alumina plates. Mass spectrum, m/z 293 for M+ of free base. (Found: C, 49.40; H, 7.13; N, 20.73. $C_{14}H_{23}N_5O_2$.HCl.0.5$H_2O$ requires C, 49.62; H, 7.44; N, 20.67%).

EXAMPLE 13

3-(3-Ethyl-1,2,4-oxadiazol-5-yl)quinuclidine Hydrogen Oxalate

The title compound free base (17 g, 77%) was prepared from methyl quinuclidine-3-carboxylate (18.0 g, 0.11 mol), propionamide oxime (14 g, 0.16 mol) and sodium hydride (7 g of a 55% oil dispersion, 0.16 mol) in anhydrous tetrahydrofuran (350 mL). The hydrogen oxalate salt had mp 113°-115° C. (propan-2-ol). $R_f$ 0.3 in dichloromethane/methanol (50:1) on alumina plates. (Found: C, 52.25; H, 6.41; N, 14.07. $C_{11}H_{17}N_3O.C_2H_2O_4$ requires C, 52.52; H, 6.44; N, 14.13%).

EXAMPLE 14

Exo-3-(3-n-Pentyl-1,2,4,-oxadiazol-5-yl)-1-azabicyclo[2.2.1]heptane p-Toluene Sulphonate The title compound free base (0.59 g, 35%) was obtained from endo ethyl 1-azabicyclo[2.2.1]heptane-3-carboxylate (1.2 g, 7.1 mmol), n-pentylcarboxyamide oxime (1.85 g, 1.4 mmol) and sodium hydride (0.62 g of a 55% oil dispersion, 1.4 mmol) in anhydrous tetrahydrofuran (110 mL). The p-toluene sulphonate salt had mp 128°–129° C. (propan-2-ol/ethyl acetate). $R_f$ 0.5 in dichloromethane/methanol (99:1) on alumina. Mass spectrum, m/z 236 for $(M+H)^+$ of free base. (Found: C, 58.94; H, 7.21; N, 10.26. $C_{13}H_{21}N_3O.C_7H_8O_3S$ requires C, 58.94; H, 7.17; N, 10.31%).

EXAMPLE 15

Exo-3-(3-(3-Methylbut-1-yl)-1,2,4-oxadiazol-5-yl)-1-azabicyclo[2.2.1]heptane p-Toluene Sulphonate The title compound free base (0.625 g, 38%) was obtained from endo ethyl 1-azabicyclo[2.2.1]heptane-3-carboxylate (1.2 g, 7.1 mmol), 3-methylbut-1-yl carboxamide oxime (1.85 g, 1.4 mmol) and sodium hydride (0.62 g of a 55% oil dispersion, 1.4 mmol) in anhydrous tetrahydrofuran (110 mL). The p-toluene sulphonate salt had mp 122°–123° C. (propan-2-ol/ethyl acetate). $R_f$ 0.5 in dichloromethane/methanol (99:1) on alumina plates. Mass spectrum, m/z 235 for $M^+$ of free base. (Found: C, 57.54; H, 6.8; N, 10.03. $C_{13}H_{21}N_3O.C_7H_8O_3S.0.5H_2O$ requires C, 57.67; H, 7.2; N, 10.08%).

EXAMPLE 16

Tablet Preparation

Tablets containing 1.0, 2.0, 25.0, 26.0, 50.0 and 100.0 mg, respectively of the following compounds are prepared as illustrated below:
3-(3-Dimethylamino-1,2,4-oxadiazol-5-yl)-5-methyl-1,2,5,6-tetrahydropyridine hydrochloride
(3R,4R)-3-(3-Cyclopropyl-1,2,4-oxadiazol-5-yl)-1-azabicyclo[2.2.1]heptane. Hydrochloride
Exo 3-(3-Dimethylamino-1,2,4-oxadiazol-5-yl)-1-azabicyclo[2.2.1]heptane Hydrochloride

| TABLE FOR DOSES CONTAINING FROM 1–25 MG OF THE ACTIVE COMPOUND | | | |
|---|---|---|---|
| | Amount-mg | | |
| Active Compound | 1.0 | 2.0 | 25.0 |
| Microcrystalline cellulose | 49.25 | 48.75 | 37.25 |
| Modified food corn starch | 49.25 | 48.75 | 37.25 |
| Magnesium stearate | 0.50 | 0.50 | 0.50 |

| TABLE FOR DOSES CONTAINING FROM 26–100 MG OF THE ACTIVE COMPOUND | | | |
|---|---|---|---|
| | Amount-mg | | |
| Active Compound | 26.0 | 50.0 | 100.0 |
| Microcrystalline cellulose | 52.0 | 100.0 | 200.0 |
| Modified food corn starch | 2.21 | 4.25 | 8.5 |
| Magnesium stearate | 0.39 | 0.75 | 1.5 |

All of the active compound, cellulose, and a portion of the corn starch are mixed and granulated to 10% corn starch paste. The resulting granulation is sieved, dried and blended with the remainder of the corn starch and the magnesium stearate. The resulting granulation is then compressed into tablets containing 1.0 mg, 2.0 mg, 25.0 mg, 26.0 mg, 50.0 mg and 100 mg of the active ingredient per tablet.

EXAMPLE 17

Eye Drops

Solution compositions for topical administration containing 1.0 mg of the compounds of the Descriptions and Examples are prepared as illustrated below:

| The pharmaceutically acceptable salt of the active compound | 0.5% |
|---|---|
| Benzalkonium chloride solution | 0.02% v/v |
| Disodium edetate | 0.05% |
| NaCl | 0.8% |
| Water for injections | to 100% |

Compound, disodium edetate, sodium chloride and benzalkonium chloride are added to and admixed with water. The final formulation is diluted to volume. The formulation is rendered sterile by appropriate means, such as starting the preparation procedure with sterile components and proceeding under sterile conditions, irradiating or autoclaving the finished formulation, or the like.

EXAMPLE 18

Ophthalmic Inserts

Ophthalmic inserts containing 1.0 mg of the following compounds are prepared as illustrated below:
3-(3-dimethylamino-1,2,4-oxadiazol-5-yl)-5-methyl-1,2,5,6-tetrahydropyridine hydrochloride;
(3R,4R)-3-(3-cyclopropyl-1,2,4-oxadiazol-5-y)1-1-azabicyclo[2.2.1]heptane hydrochloride;
exo3-(3-dimethylamino-1,2,4-oxadiaxol-5-yl)-1-azabicyclo[2.2.1]heptane hydrochloride.

| Active compound | 1 mg |
|---|---|
| Hydroxypropylcellulose q.s. | 12 mg |

Ophthalmic inserts are manufactured from compression moulded films which are prepared on a Carver Press by subjecting the powdered mixture of the above ingredients to a compressional force of 12,000 lbs (gauge) at 300° F. for one to four minutes. The film is cooled under pressure by having cold water circulate in the platen. Ophthalmic inserts are then individually cut from the film with a rod-shaped punch. Each insert is placed into a vial, which is then placed in a humidity cabinet (88% R.H. at 30° C.) for two or four days. After removal from the humidity cabinet, the vials are stoppered and then capped. The vials containing the hydrate insert are then autoclaved at 250° F. for ½ hour.

METHOD FOR BIOLOGICAL ACTIVITY

Male or female African Green monkeys (2.0–4.5 kg) were fasted following their afternoon feeding on the day prior to the experiment. The monkeys were anaesthestised in their cages with approximately 10 mg/kg i.m. ketamine HCl (Vetalar or Ketaset). Once sedated, the animals were restrained in monkey chairs and brought to the laboratory. One drop of 0.5% proparacaine HCl (Ophthetic) was instilled into each eye. After 30 seconds, intraocular pressure (IOP) determinations were taken in each eye (control or "0" time reading) using a Digilab Modular One Pneuma Tonometer. Both eyes were then flushed with saline. Vehicle or test agent (0.0005-2.0%) was administered (25 μl) into the cul-de-sac of both eyes and the IOP was determined at 0.5 and 1.0 hour and at hourly intervals thereafter for up to 5 hours and compared to the control IOP. For ocular instillation, 0.5% hydroxyethylcellulose (HEC) was employed as the vehicle. Supplemental doses of 10 mg or more/animal i.m. ketamine HCl were given 3-5 minutes prior to IOP determinations. Proparacaine HCl (0.5% (one drop/eye) was also instilled immediately prior to IOP determinations. Following the final IOP determination, both eyes were flushed liberally with saline and a sterile ophthalmic ointment (Ilotycin, erythromycin, 5 mg/gm) was applied. Animals were allowed to recover in their cages and a light meal was provided. At least 2 days separated individual intraocular pressure experiments.

Pupil diameter was measured under standard laboratory lighting conditions using a millimeter ruler. ["Vetalar," "Ketaset", "Ophthetic", "Digilab Modular One" and "Ilotycin" are all trade marks.]

| BIOLOGICAL ACTIVITY | | |
|---|---|---|
| Compound of | Concentration | Change in IOP[a] |
| Description A | 0.0005% | −6 |
| Description B | 0.005% | −5 |
| Description C | 0.05% | −5 |
| Description D | 0.05% | −3 |
| Description E | 0.05% | −3 |
| Description F | 0.5% | −2 |
| Description G | 1.5% | −4.5 |
| Description H | 2.0% | −1.5 |
| Description I | 2.0% | −4.5 |
| Description J | 0.05% | −3 |
| Description K | 0.5% | −3.5 |
| Description L | 0.5% | −2.5 |
| Description M | 0.5% | −3.5 |
| Description N | 0.5% | −2.5 |
| Example 1 | 0.05% | −5 |
| Example 2 | 0.10% | −5 |
| Example 3 | 2.0% | −5 |
| Example 4 | 0.005% | −4 |
| Example 5 | 0.005% | −2 |
| Example 6 | 0.5% | −3 |
| Example 7 | 0.05% | −2 |
| Example 8 | 2.0% | −5 |
| Example 9 | 2.0% | −3 |
| Example 10 | 2.0% | −3.5 |
| Example 11 | 0.5% | −3 |
| Example 12 | 0.05% | −3 |
| Example 13 | 2.0% | −3 |
| Example 14 | 2.0% | −2 |
| Example 15 | 0.5% | −2 |

FOOTNOTE: [a]Maximum mm Hg change in intraocular pressure

What is claimed is:

1. A method for the treatment of glaucoma or for reducing intraocular pressure said method comprising the administration to a patient in need of such treatment an intraocular pressure reducing amount of at least one compound selected from compounds of formula (I):

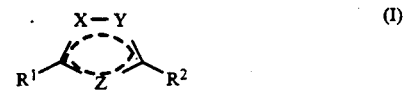

wherein
one of X, Y, or Z is an oxygen or sulphur atom and the other two are nitrogen atoms, and the dotted circle represent two double bonds thus forming a 1,3,4-oxadiazole; 1,2,4-oxadiazole; 1,3,4-thiadiazole or 1,2,4-thiadiazole nucleus;

$R^1$ represents a non-aromatic azacyclic or azabicyclic ring system selected from

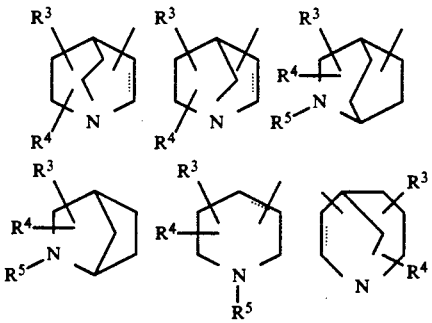

wherein the broken line represents an optional chemical bond;
the substituents $R^3$ and $R^4$ may be present at any position, including the point of attachment to the oxa- or thia-diazole ring, and are each independently selected from a member of the group consisting of hydrogen, $C_{1-4}$ alkyl, halo, $C_{1-4}$ alkoxy, hydroxy and carboxy, or $R^3$ and $R^4$ together represent carbonyl;
the group $R^5$ is selected from hydrogen and $C_{1-4}$ alkyl; and
$R^2$ is selected from hydrogen, $C_{1-8}$ alkyl optionally substituted by hydroxy or fluoro, $C_{2-8}$ alkenyl, $OR^7$, $SR^7$, $NR^7R^8$, CN, $CO_2R^7$, $CONR^7R^8$ and $NHCONHR^9$ where $R^9$ is a $C_{1-4}$ alkyl;
wherein $R^7$ and $R^8$ are each independently selected from hydrogen and saturated and unsaturated $C_{1-8}$ alkyl provided that, when $R^7$ and $R^8$ in $NR^7R^8$ are both hydrogen, at least one of $R^3$ and $R^4$ is $C_{1-4}$ alkyl, and salts thereof.

2. The method according to claim 1, wherein the compound is selected from compounds of formula (II):

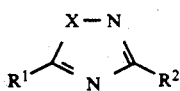

wherein $R^1$, $R^2$ and X are as defined for formula (I).

3. The method according to claim 2 wherein $R^1$ is selected from 1,2,5,6-tetrahydropyridinyl optionally substituted on the ring nitrogen with methyl or ethyl, 1-azabicyclo[2.2.1]heptanyl, 2-azabicyclo[2.2.2]octanyl and quinuclidinyl.

4. The method according to claim 3, wherein $R^3$ and $R^4$ are selected from the group consisting of hydrogen, hydroxy and $C_{1-4}$ alkyl.

5. The method according to claim 3, wherein $R^5$ is selected from they group consisting of hydrogen, methyl and ethyl.

6. The method according to claim 2 wherein $R^2$ is $C_{1-8}$ alkyl, optionally substituted by a member of the group selected from OH and F or $R^2$ is $NR^7R^8$ when $R^7$ is hydrogen or saturated or unsaturated $C_{1-3}$ alkyl, and $R^8$ is saturated or unsaturated $C_{1-3}$ alkyl.

7. The method according to claim 6, wherein $R^2$ is selected from the group consisting of methyl, ethyl, cyclopropyl, methylamino, dimethylamino and dipropargylamino.

8. The method according to claim 1, wherein the compound is selected from compounds of formula (III):

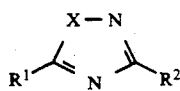

wherein
$R^1$ is selected from 1,2,5,6-tetrahydropyridyl (optionally substituted on the ring nitrogen with methyl or ethyl), 1-azabicyclo[2.2.1]heptanyl, 2-azabicyclo[2.2.2] octanyl (isoquinuclidinyl), quinuclidinyl and piperidyl;

$R^3$ and $R^4$ are selected from the group consisting of hydrogen, hydroxy and $C_{1-4}$ alkyl;

$R^5$ is selected from the group consisting of hydrogen, methyl and ethyl;

$R^2$ is $C_{1-8}$ alkyl, optionally substituted by a member selected from the group consisting of OH and F, $C_{2-8}$ alkenyl, $NR^7R^8$ and $CONR^7R^8$ when $R^7$ is selected from hydrogen, saturated and unsaturated $C_{1-3}$ alkyl, and $R^8$ is selected from hydrogen, saturated and unsaturated $C_{1-3}$ alkyl, and $NHCONHR^9$ where $R^9$ is $C_{1-4}$ alkyl, and salts thereof.

9. A method of treatment of glaucoma which comprises administering to a patient in need of such treatment an effective amount of a compound selected from:
3-(3-dimethylamino-1,2,4-oxadiazol-5-yl)-5-methyl-1,2,5,6-tetrahydropyridine;
exo-3-(3-dimethylamino-1,2,4-oxadiazol-5-yl)-1-azabicyclo-[2.2.1]heptane;
3-(3-methylamino-1,2,4-oxadiazol-5-yl)-1,2,5,6-tetrahydropyridine;
3-(3-dimethylamino-1,2,4-oxadiazol-5-yl)-1,2,5,6-tetrahydropyridine;
3-(3-dimethylamino-1,2,4-oxadiazol-5-yl)-1-methyl-1,2,5,6-tetrahydropyridine;
3-(3-dipropargylamino-1,2,4-oxadiazol-5-yl)-1,2,5,6-tetrahydropyridine;
3-(3-methyl-1,2,4-oxadiazol-5-yl)-1-ethyl-1,2,5,6-tetrahydropyridine;
3-(3-cyclopropyl-1,2,4-oxadiazol-5-yl)-1,2,5,6-tetrahydropyridine;
exo-3-(3-cyclopropyl-1,2,4-oxadiazol-5-yl)-1-azabicyclo[2.2.1]heptane;
Anti-6-(3-ethyl-1,2,4-oxadiazol-5-yl)-2-azabicyclo[2.2.2]octane;
(−)-Anti-6-(3-ethyl-1,2,4-oxadiazol-5-yl)-2-azabicyclo[2.2.2]octane;
Endo-3-(3-cyclopropyl-1,2,4-thiadiazol-5-yl)-1-azabicyclo[2.2.1]heptane;
Endo-3-(3-dimethylamino-1,2,4-thiadiazol-5-yl)-1-azabicyclo[2.2.1]heptane;
(3R,4R)-3-(3-cyclopropyl-1,2,4-oxadiazol-5-yl)-1-azabicyclo[2.2.1]heptane;
3-(3-dimethylamino-1,2,4-oxadiazol-5-yl)-1,5-dimethyl-1,2,5,6-tetrahydropyridine;
3-(3-ethyl-1,2,4-oxadiazol-5-yl)-1,5-dimethyl-1,2,5,6-tetrahydropyridine;
3-(3-methyl-1,2,4-oxadiazol-5-yl)-5-dimethyl-1,2,5,6-tetrahydropyridine;
3-(3-methyl-1,2,4-oxadiazol-5-yl)-1,5-dimethyl-1,2,5,6-tetrahydropyridine;
Exo-3-(3-cyclopropyl-1,2,4-oxadiazol-5-yl)-endo-5-hydroxy-1-azabicyclo[2.2.1]heptane;
Exo-3-(3-dimethylamino-1,2,4-thiadiazol-5-yl)-endo-5-hydroxy-1-azabicyclo[2.2.1]heptane;
Exo-3-(3-isopropyl-1,2,4-thiadiazol-5-yl)-endo-5-hydroxy-1-azabicyclo[2.2.1]heptane;
3-(3-carboxamide-1,2,4-oxadiazol-5-yl)quinuclidine;
Exo-3-(3-isopropyl-1,2,4-oxadiazol-5-yl)-1-azabicyclo[2.2.1]heptane;
3-(3-ethenyl-1,2,4-oxadiazol-5-yl)-1,2,5,6-tetrahydropyridine;
3-(3-ethyl-1,2,4-oxadiazol-5-yl)piperidine;
3-(3-t-butylaminocarbonylamino-1,2,4-oxadiazol-5-yl)quinuclidine;
3-(3-ethyl-1,2,4-oxadiazol-5-yl)quinuclidine;
Exo-3-(3-n-pentyl-1,2,4-oxadiazol-5-yl)-1-azabicyclo[2.2.1]heptane;
Exo-3-3-methylbut-1-yl)-1,2,4-oxadiazol-5-yl)-1-azabicyclo[2.2.1]heptane;
and salts thereof.

* * * * *